United States Patent [19]

Yarrow et al.

[11] 4,289,764

[45] Sep. 15, 1981

[54] STEROID COMPOSITIONS

[75] Inventors: Hyman Yarrow, Hitchin; Martin Whitefield, London, both of England

[73] Assignee: Drythanol Ltd., London, England

[21] Appl. No.: 100,038

[22] Filed: Dec. 4, 1979

[51] Int. Cl.³ .................... C07J 7/00; A61K 31/56
[52] U.S. Cl. ............................................ 424/243
[58] Field of Search ........................................ 424/243

[56] References Cited

U.S. PATENT DOCUMENTS 3,899,580  8/1975  O'Neill et al. ................... 424/243

*Primary Examiner*—Elbert L. Roberts
*Attorney, Agent, or Firm*—Stevens, Davis, Miller & Mosher

[57] ABSTRACT

The invention provides a pharmaceutical composition for topical application comprising an essentially saturated solution of hydrocortisone in aqueous propylene glycol solution containing at least 15% but less than 50% by weight of propylene glycol, the proportion of hydrocortisone in the total composition being at least 0.08% but not greater than 0.4% by weight of aqueous propylene glycol and from 0.025 to 0.4% based on the total weight of the composition, the said composition being characterized by a pH in the range of 2.7 to 3.3, and the substantial absence of metallic cations. Such compositions have excellent storage stability and surprisingly high effectiveness of the hydrocortisone contained therein.

4 Claims, No Drawings

STEROID COMPOSITIONS

DESCRIPTION

This invention relates to steroid compositions for topical application.

In our British Specification No. 1543907, we have described a novel kind of formulation of hydrocortisone which has a much improved effectiveness as compared with previously known hydrocortisone-containing compositions. The compositions of our aforesaid Specification comprise an essentially saturated (i.e. saturated at the lowest temperature to which the composition is likely to be subjected during use or storage, e.g. 0° C.) solution of hydrocortisone in an aqueous propylene glycol solution containing at least 15% but less than 50% by weight of propylene glycol and having a pH 4.5-5, the proportion of hydrocortisone in the total composition being at least 0.08% but not greater than 0.4% by weight of the aqueous propylene glycol and from 0.025 to 0.4% based on the total weight of the composition. Such compositions containing 0.1% of hydrocortisone are more effective than hydrocortisone cream BP containing 1% hydrocortisone in the McKenzie & Stoughton vasoconstriction test (Arch. Derm. 86, 608, 1962).

During the last two or three years a new method of hydrocortisone assay applicable to pharmaceutical compositions and based on the use of high pressure liquid chromatography has been introduced. This method has shown that the previously used colorimetric method of hydrocortisone assay has the serious drawback that some hydrocortisone degradation products give the same colour reaction as hydrocortisone itself. Consequently the new method has revealed instability problems with some known hydrocortisone-containing compositions, particularly those which are aqueous and including the composition described in our aforesaid British Specification. While at temperatures below 15° C., the aforesaid composition has satisfactory storage stability at higher temperatures it has a relatively limited shelf life.

It has now surprisingly been discovered that by very careful and precise alteration of the pH and constituents of the aforesaid compositions it is possible to produce a novel hydrocortisone-containing steroid composition which has a substantially improved storage stability, and very surprisingly an even higher activity than the compositions described in our aforesaid Specification.

The compositions of the present invention comprise an essentially saturated solution of hydrocortisone in an aqueous propylene glycol solution containing at least 15% but less than 50% by weight of propylene glycol, the proportion of hydrocortisone in the total composition being at least 0.08% but not greater than 0.4% by weight of the aqueous propylene glycol and from 0.025 to 0.4% based on the total weight of the composition, the composition being substantially free of metallic cations and containing sufficient of a pharmacologically acceptable compatible non-toxic acid to bring the pH to within the range 2.7 to 3.3. Very surprisingly, these novel compositions show a higher degree of activity than the composition described in our aforesaid Specification (which has a pH of 5), a substantially higher activity than an otherwise similar composition having a pH of 2.5, and a higher activity than a similar composition containing appreciable amounts of a metallic cation such as sodium ions (which are of course a frequent constituent of known buffering systems). Moreover, the new formulation has substantially superior storage stability as compared with the formulation described in our aforesaid Specification.

The proportions of water and propylene glycol in the new compositions are, as in the case of the compositions described in our aforesaid Specification, very important. About 50% by weight of propylene glycol based on the weight of aqueous propylene glycol solution, the hydrocortisone is not sufficiently rapidly released by the composition onto the skin to be very effective, and the concentration of hydrocortisone required for saturation is uneconomically high, while below 15% by weight propylene glycol (corresponding to a saturated solution of hydrocortisone in aqueous propylene glycol containing 0.08% by weight of hydrocortisone), the saturated concentration of hydrocortisone in the aqueous propylene glycol is too low for a satisfactory effect. The solvent therefore contains at least 15% but less than 50%, preferably about 33%, by weight of propylene glycol, the balance being water.

Because aqueous propylene glycol has a low viscosity, it is usually convenient to incorporate into the new composition some kind of thickener. Preferred thickeners are long-chain paraffins, fatty alcohols, and waxes, sufficient of the thickener being incorporated in the composition to give the desired viscosity. Examples of suitable materials are cetostearyl alcohol, white soft paraffin, and liquid paraffin. The ointment base called Emulsifying Ointment (British Pharmacopoea) is especially convenient. It contains a small porportion of sodium lauryl sulphate, but not however enough to have a disadvantageous effect, at least when, as is preferred, the acid used is one capable of chelating metallic cations.

The proportion of hydrocortisone in the new compositions is from 0.025 to 0.4%, preferably 0.05 to 0.3%, by weight of the total composition. The proportion of hydrocortisone in the total composition based on the weight of aqueous propylene glycol must be at least 0.08% but not greater than 0.4%. For most uses, good results are obtained with a hydrocortisone concentration in the total composition of about 0.1% by weight of the total composition, and of 0.167% by weight of the aqueous propylene glycol.

Any pharmacologically acceptable compatible non-toxic acidic material may be used to bring the pH of the composition to within the range of 2.7 to 3.3. It should be borne in mind in this connection that the amount of acid used should not be so great that after application of the composition to the skin the pH is still held at 2.7 to 3.3 rather than the normal physiological pH of the skin. Non-toxic organic carboxylic acids which are sufficiently acidic to achieve the desired pH when used in small amount are preferably used. Since acids by themselves are not buffers it is difficult to ensure that a precisely fixed pH is always obtained because of slight variations in the quality of the ingredients used. However if the proportions of the ingredients used are such as to give in most cases a pH of 2.8 to 3.0, it will only rarely be found that the pH obtained is outside the desired range of 2.7 to 3.3. Because of the possibility that some of the ingredients used may contain small amounts of metallic cations (e.g. the sodium ions in Emulsifying Ointment BP already mentioned), it is preferred to use an acid which has the ability to chelate metallic cations, i.e. is also a chelating agent. Citric acid is particularly well suited for this purpose, and a concentration of about 0.167% based on the aqueous propylene glycol normally gives a pH within the desired range.

An anti-bacterial agent may if desired be included in the composition in an appropriate concentration.

The following Example illustrates the invention.

EXAMPLE

Hydrocortisone (0.1 g) was dissolved in propylene glycol (20 g). Separately citric acid (0.1 g) was dissolved in deionised water (40 g). The two solutions were warmed to 60° C. and then mixed. This mixture was then poured into emulsifying ointment BP (37.9 g) which had previously been melted at 60° C. The composition was stirred until cool. The emulsifying ointment forms a discontinuous phase in the aqueous propylene glycol. The citric acid adjusts the pH of the composition to 2.8.

This formulation has been compared for storage stability with that described in our aforesaid British Specification No. 1543907. Samples of the two compositions were stored at ambient temperature (about 20° C.) or at 40° C. for periods up to 13 months, and were periodically analysed during the storage period for their hydrocortisone content. The following results were obtained:

| Composition | Temperature | Storage Period | % Hydrocortisone (original = 100%) |
|---|---|---|---|
| Composition of the present invention | Ambient | 6 weeks | 102.3 |
| | " | 3 months | 101.4 |
| | " | 6 months | 104.1 |
| | " | 9 months | 98.6 |
| | " | 13 months | 98.6 |
| Composition of the present invention | 40° C. | 6 weeks | 98.7 |
| | " | 3 months | 95.0 |
| | " | 6 months | 89.1 |
| | " | 9 months | 80.9 |
| Composition of British Specification No. 1543907 | Ambient | 6 weeks | 93.2 |
| | " | 3 months | 91.8 |
| | " | 6 months | 90.0 |
| | " | 9 months | 80.9 |
| | " | 13 months | 70.5 |
| Composition of British Specification No. 1543907 | 40° C. | 6 weeks | 70.5 |
| | " | 3 months | 52.3 |
| | " | 6 months | 29.5 |
| | " | 9 months | 13.6 |

These figures clearly show the superior storage stability of the formulation in accordance with the present invention. The prior composition had to be stored at 15° C. or below in order to achieve satisfactory shelf life. The composition of the present invention, on the other hand, can be stored safely at ambient temperature or even slightly above.

In a series of tests based on the above-mentioned McKenzie & Stoughton vasoconstriction test, the aforesaid composition in accordance with the present invention was compared with a number of similar compositions including the composition described in our aforesaid British Specification No. 1543907. The results obtained showed that the composition in accordance with the present invention was, in this test, at least twice as active as the composition of our prior Specification. Similar compositions having a pH of about 3.2 but containing sodium dihydrogen phosphate were significantly less active than the composition of the present invention unless the hydrocortisone content is raised to 0.25%. On the other hand, a composition having a pH of 2.5 and containing 0.1% of hydrocortisone was substantially less active than the composition of the present invention and indeed less active than the composition of the prior Specification. It is thus critically necessary to keep within the above specified pH range and to keep down the concentration of metallic cations in order to achieve the superior activity of the compositions of the present invention.

We claim:

1. In a pharmaceutical composition for topical application comprising an essentially saturated solution of hydrocortisone in an aqueous propylene glycol solution containing at least 15% but less than 50% by weight of propylene glycol, the proportion of hydrocortisone in the total composition being at least 0.08% but not greater than 0.4% by weight of aqueous propylene glycol and from 0.025 to 0.4% based on the total weight of the composition, the improvement which consists in including in the composition sufficient of a pharmacologically acceptable compatible non-toxic acid to bring the pH of the composition to within the range 2.7 to 3.3, and in substantially excluding metallic cations from the composition.

2. The improvement of claim 1 in which the said acid is an aqueous carboxylic acid which is also a chelating agent.

3. The improvement of claim 1 in which the said acid is citric acid.

4. A pharmaceutical composition for topical application consisting essentially of hydrocortisone 0.05 to 0.3%, propylene glycol about 20%, emulsifying ointment BP about 40%, water about 40%, and sufficient citric acid to adjust the pH to 2.7 to 3.3.

* * * * *